United States Patent [19]

Fischer

[11] Patent Number: 5,006,113
[45] Date of Patent: Apr. 9, 1991

[54] HEMOSTASIS CANNULA

[75] Inventor: Frank Fischer, Bloomington, Ind.

[73] Assignee: Cook Incorporated, Bloomington, Ind.

[21] Appl. No.: 510,591

[22] Filed: Apr. 17, 1990

Related U.S. Application Data

[63] Continuation-in-part of Ser. No. 477,345, Feb. 8, 1990, which is a continuation-in-part of Ser. No. 357,041, May 25, 1989, abandoned.

[51] Int. Cl.$^5$ .......................................... A61B 5/178
[52] U.S. Cl. .................................................. 604/167
[58] Field of Search ............... 604/167, 158, 169, 264, 604/256, 247, 246, 280

[56] References Cited

U.S. PATENT DOCUMENTS

| | | |
|---|---|---|
| 2,023,267 | 12/1935 | De Saint-Rapt et al. |
| 3,853,127 | 12/1974 | Spademan |
| 4,000,739 | 1/1977 | Stevens |
| 4,143,853 | 3/1979 | Abramson |
| 4,177,814 | 12/1979 | Knepshield et al. |
| 4,334,551 | 6/1982 | Pfister |
| 4,412,836 | 11/1983 | Brignola |
| 4,430,081 | 2/1984 | Timmermans |
| 4,436,519 | 3/1984 | O'Neill |
| 4,475,548 | 10/1984 | Muto |
| 4,496,348 | 1/1985 | Genese et al. |
| 4,610,665 | 9/1986 | Matsumoto et al. |
| 4,610,674 | 9/1986 | Suzuki et al. |
| 4,626,245 | 12/1986 | Weinstein |
| 4,634,432 | 1/1987 | Kocak |
| 4,657,772 | 4/1987 | Kocak |
| 4,705,511 | 11/1987 | Kocak |
| 4,798,594 | 1/1989 | Hillstead |

*Primary Examiner*—John D. Yasko
*Attorney, Agent, or Firm*—Woodard, Emhardt, Naughton, Moriarty & McNett

[57] ABSTRACT

A hemostasis cannula includes a main body defining a passage therethrough adapted to receive a catheter. The main body has externally threaded surfaces adjacent the ends of the body to receive a cap and an end retainer threaded thereon. The cap is an open-ended cap with an opening in the top of the cap to receive the catheter. Clamped between the cap and the main body is a flexible, resilient disk-like gasket. The gasket includes an upper elongated slit extending diametrically across the top surface of the gasket and extending through the outer perimetrical edge surface of the gasket. A lower elongated slit extends diametrically across the lower surface and through the outer perimetrical surface. Both slits are cut into the gasket to a predetermined depth without passing entirely through the thickness of the gasket. In one embodiment illustrated, the slits are arranged to intersect within the interior of the gasket to provide an opening for insertion of the catheter. In another embodiment illustrated, the slits do not intersect each other, but instead have collective depths less than the thickness of the gasket. A generally axial opening is provided between the two slits. A flexible tube is affixed to the main body of the cannula by the end retainer. The flexible tube is constructed to include an inner tube with a coil body surrounding the inner tube substantially along the length of the tube. A sheath surrounds the coil body. The flexible tube thus configured resists crimping, kinking and buckling when the tube is subject to bending. The hemostasis cannula and particularly the gasket provides a leak-proof seal to prevent the flow of blood from or air into a blood vessel.

22 Claims, 4 Drawing Sheets

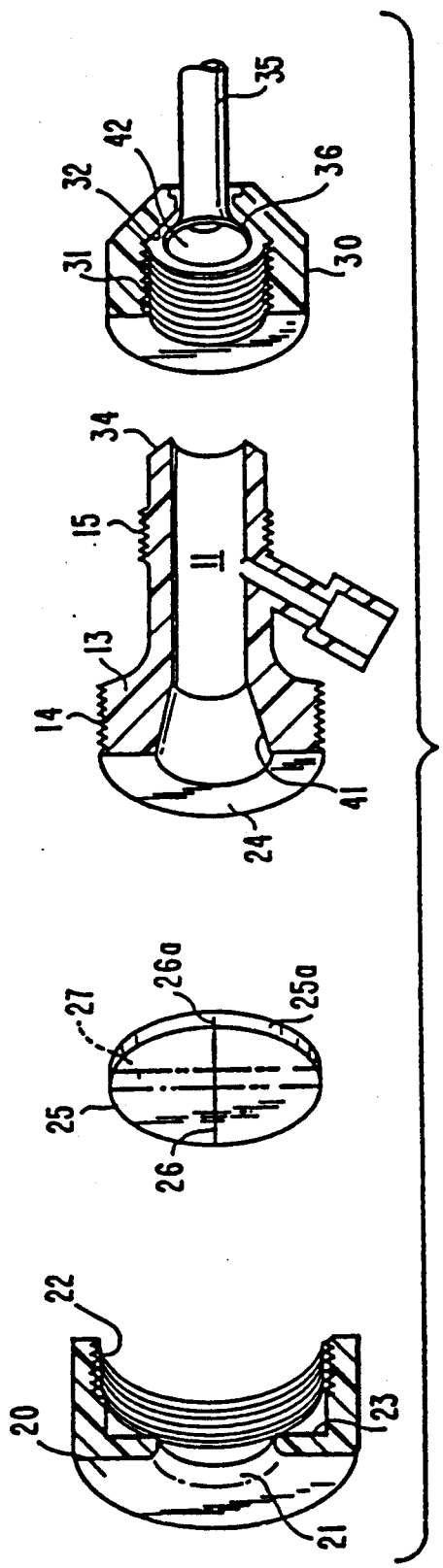
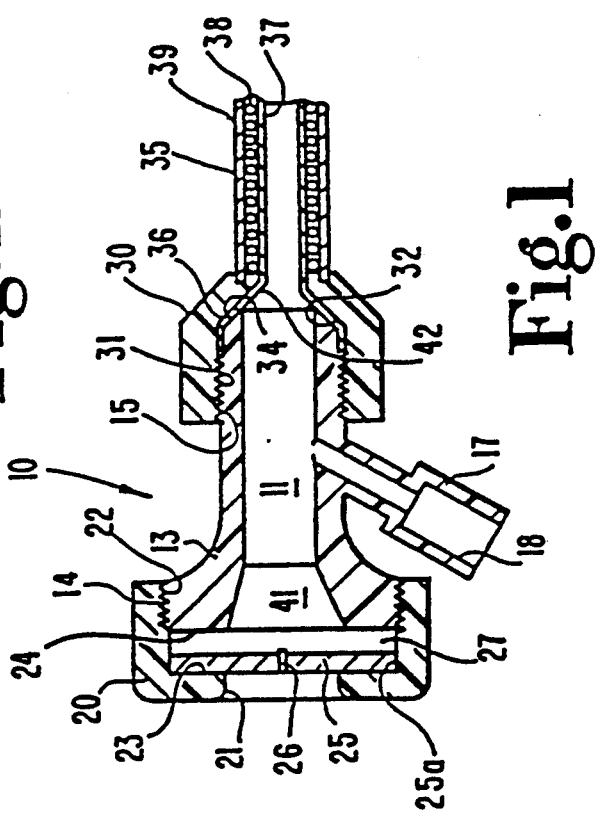
Fig.1
Fig.2

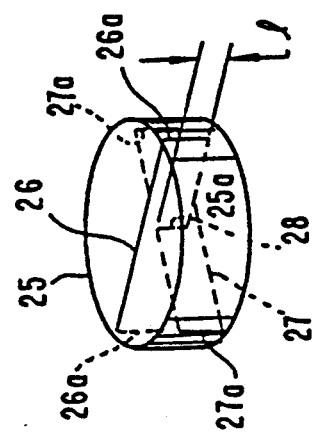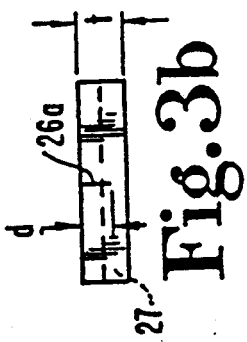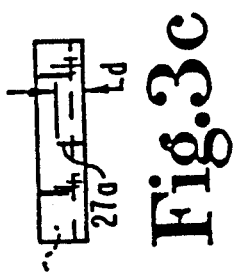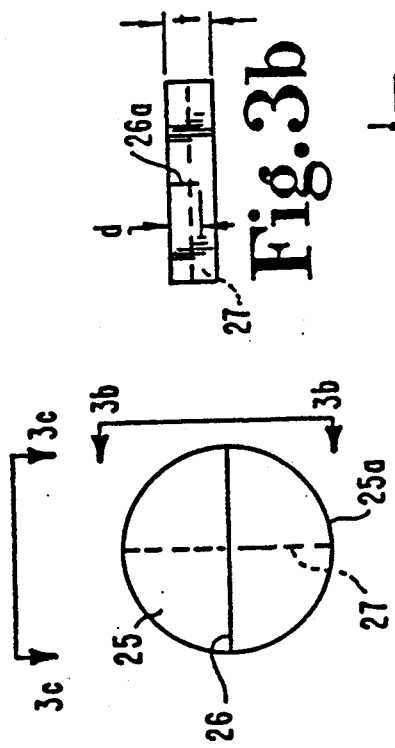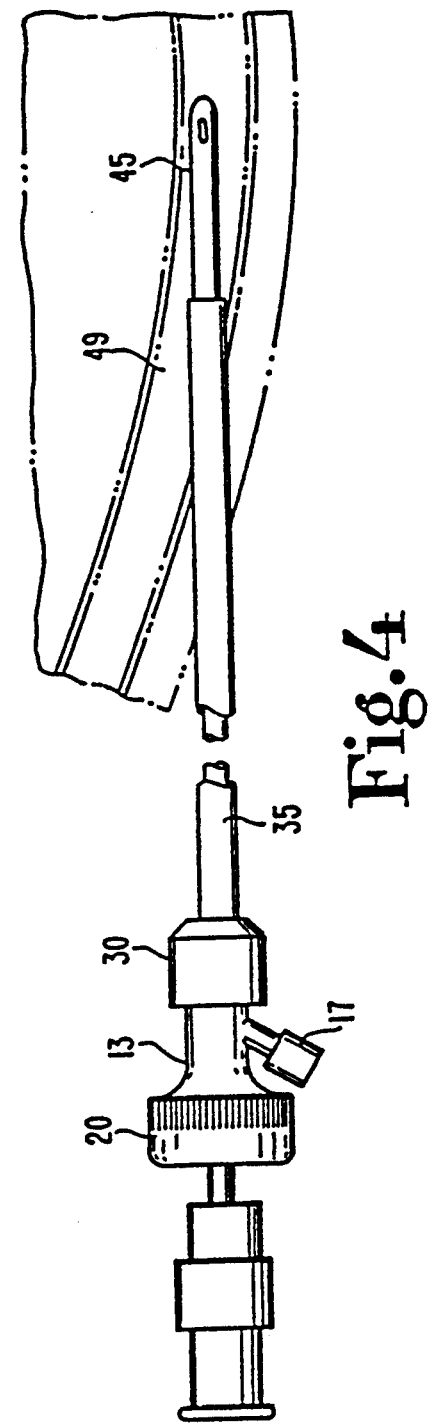

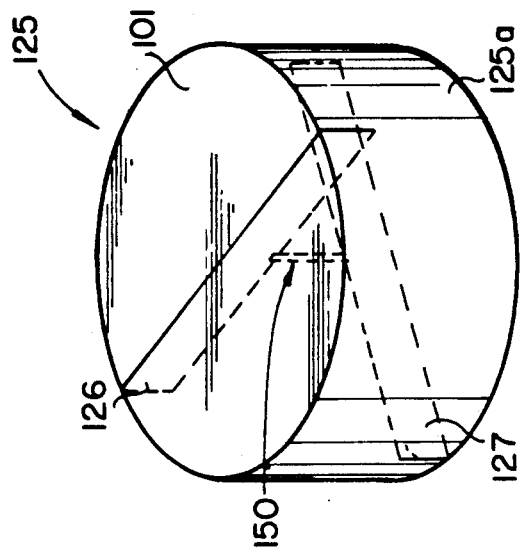
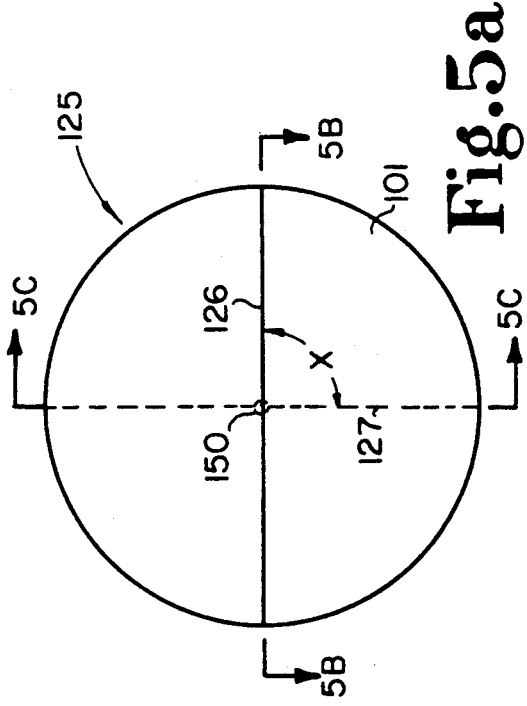
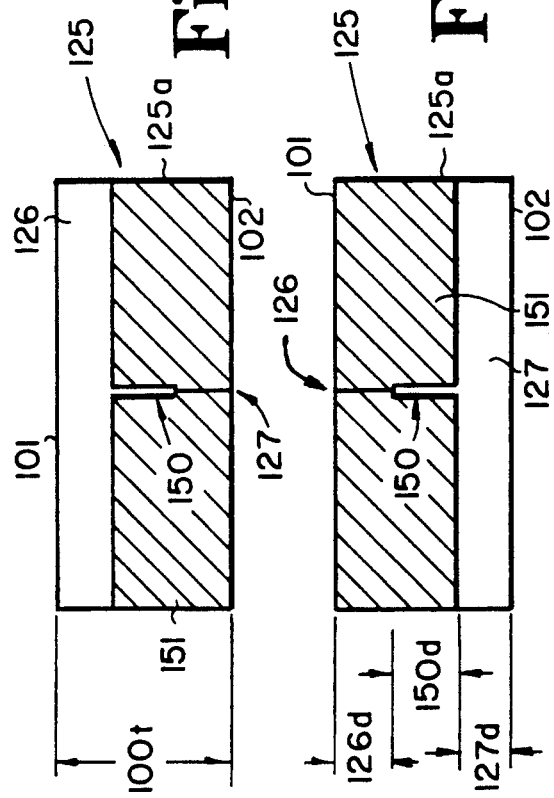

HEMOSTASIS CANNULA

REFERENCE TO RELATED APPLICATIONS

This application is a continuation-in-part of U.S. patent application Ser. No. 477,345, filed on Feb. 8, 1990, which is a continuation-in-part of U.S. patent application Ser. No. 357,041, filed on May 25, 1989 now abandoned by the same inventive entity, and entitled HEMOSTASIS CANNULA.

BACKGROUND OF THE INVENTION

This invention relates to a cannula or sheath and particularly to a cannula usable with angiographic catheters.

In certain angiographic studies, the angiographer uses the Desilets-Hoffman procedure to do a multiple study. In this procedure, the angiographer obtains access to a patient's blood vessel by inserting a hollow needle through the skin and into the lumen of the blood vessel. A guidewire is passed through the needle and advanced through the artery or vein into the organ to be studied. The needle is removed leaving the guidewire in the organ. A cannula and dilator are advanced over the wire into the vessel and the dilator is removed along the guidewire. The angiographer can then conduct the multiple studies by inserting various types of catheters into the vessel through the cannula or sheath.

In order to avoid excessive bleeding and to insure against the possibility of an air embolism, this technique requires occlusion of the passage through the cannula during catheter changes. When such occluding is performed manually there is always the possibility that it will not be accomplished as quickly as desired and will not be continuously effective for as long as desired. In one type of prior art hemostasis cannula, represented by the Stevens U.S. Pat. No. 4,000,739, a cannula valve is provided that is only intended to prevent blood loss from the vessel.

However, it is also desirable that the cannula valve be effective in preventing air flow into the blood vessel. The patent to Timmermans, U.S. Pat. No. 4,430,081, shows a cannula valve adapted to be effective in preventing both blood loss from and air flow into the blood vessel. The Timmermans cannula valve employs a first, second and third disk-like gasket mounted in the cannula passage. The patent to Suzuki, et al., U.S. Pat. No. 4,610,674, shows a catheter introducing instrument in which the introducer valve includes a single flexible disk having a pair of intersecting incisions formed from the top and bottom surfaces of the disk. However, the Suzuki introducer valve generally is not adapted to permit easy introduction and manipulation of larger diameter catheters.

SUMMARY OF THE INVENTION

It is therefore an object to provide a hemostasis cannula that positively seals against leakage of air or fluids into or out of a body passageway or blood vessel. It is a further object to provide a cannula that protects against such leakage whether or not a catheter is introduced in the cannula. Yet another object is to provide a cannula that is adapted for use with relatively larger catheters.

These and other objects and benefits are satisfied by a hemostasis cannula comprising a body having an elongated passage therethrough adapted to receive a catheter. Mounted in the passage at one end of the passage is a disk-like gasket that includes opposite first and second surfaces and an outer edge surface between the first and second surfaces. An elongated first slit extends across the first surface and into the gasket toward the second surface without passing entirely therethrough. An elongated second slit extends across the second surface and into said gasket toward the first surface without passing entirely therethrough. The ends of the both slits may pass completely through the outer edge surface. The first and second slits are formed shallow enought with respect to the thickness of the gasket so as to not intersect each other within the gasket. A generally axial opening is provided between the first and second slits, providing a sealable path for the insertion of a catheter. The hemostasis cannula further comprises a length of flexible tubing in fluid-tight engagement with the body and communicating with the other end of the passageway. The tubing includes an enclosed coil body extending substantially along the length of the tubing and adapted to permit bending of the tubing without crimping, kinking or buckling.

BRIEF DESCRIPTION OF THE DRAWINGS

FIG. 1 is a cross-sectional view taken axially of a first embodiment of a hemostasis cannula.

FIG. 2 is an exploded partially cutaway view of the embodiment of FIG. 1.

FIG. 3a is an elevational view of the cannula valve gasket of the cannula of FIG. 1.

FIG. 3b is a side view of the cannula valve gasket taken along line 3b—3b of FIG. 3a as viewed in the direction of the arrows.

FIG. 3c is another side view of the cannula valve gasket taken along line 3c—3c of FIG. 3a as viewed in the direction of the arrows.

FIG. 3d is a perspective view of the cannula valve gasket of FIG. 3a.

FIG. 4 is a side elevational view of the cannula shown in position in the lumen of a blood vessel with a catheter extending therethrough.

FIG. 5a is an elevational view of the cannula valve gasket of the present invention.

FIG. 5b is a cross-sectional view of the cannula valve gasket taken along line 5b—5b of FIG. 5a as viewed in the direction of the arrows.

FIG. 5c is another cross-sectional view of the cannula valve gasket taken along line 5c—5c of FIG. 5a as viewed in the direction of the arrows.

FIg. 5d is a perspective view of the cannula valve gasket of the present invention.

DESCRIPTION OF THE PREFERRED EMBODIMENTS

Figure 7:
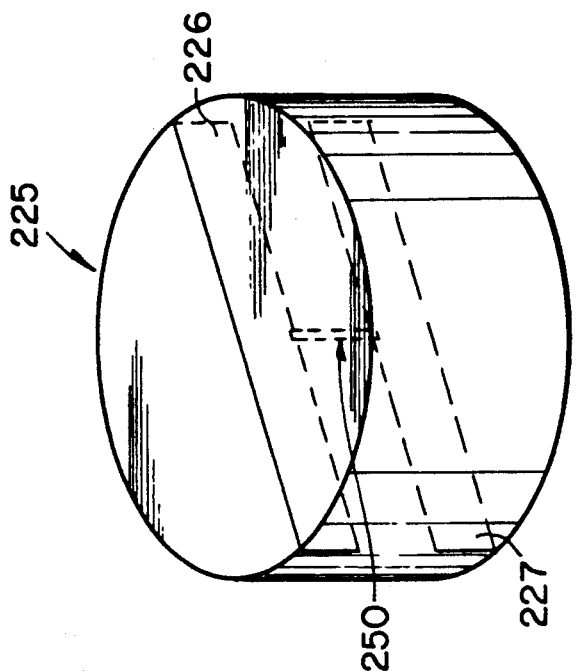
FIG. 7 is a perspective view of another embodiment of the cannula valve gasket of the present invention.
Figure 6:
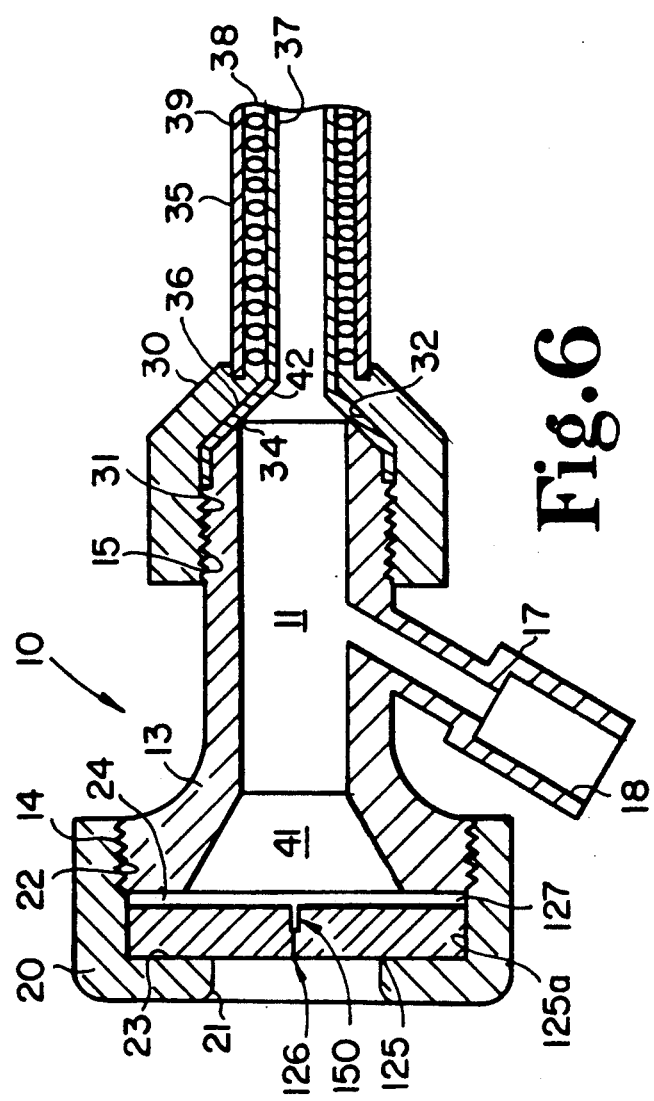
FIG. 6 is a cross-sectional view taken axially of a second embodiment of a hemostasis cannula according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

In FIG. 1 there is illustrated a hemostasis cannula 10 which includes a passage 11 therethrough adapted to receive a catheter. The cannula 10 includes a main body 13 having externally threaded surfaces 14 and 15 adjacent the ends of the body. The main body 13 further includes an extension 17 projecting outward from the side wall of the main body which includes a secondary inlet port 18. The secondary inlet port 18 communicates with the passage 11 to provide a means for medical infusion or other secondary procedures.

The cannula 10 further includes a hollow open-ended cap 20 that includes an opening 21 through the top of the cap and internal threads 22 at the open end of the cap. The internal threads 22 are adapted to engage the threads 14 of the main body 13 as the cap is threaded down on the main body. Preferably, the cap 20 is glued in place by a suitable cement or the like. Disposed between the cap 20 and the main body 13 is a flexible and elastic disk-like gasket 25. The gasket 25, shown more clearly in FIGS. 3a-3d, has an unstressed or free thickness "t" large enough so that the gasket is compressed between the cap 20 and the main body 13 when the cap is threaded down on the body. The gasket 25 is compressed adjacent the outer edge surface 25a of the gasket between a clamping surface 23 on the cap and a clamping surface 24 on the main body.

The gasket 25 includes an upper slit 26 that extends completely diametrically across the top surface of the gasket and is cut into the gasket material to a depth d, as shown in FIG. 3b. The upper slit 26 opens at slits 26a on the outer perimetrical edge surface 25a of the gasket. A second slit 27 is cut to the depth "d" from the bottom surface of the gasket upward toward the top surface and opens at slits 27a on the outer edge surface 25a. Neither of the slits 26 or 27 is cut completely through the thickness "t" of the gasket 25, and preferably the depth "d" is approximately ⅔ the thickness "t". The lower slit 27 is cut transversely to the upper slit 26 so that the upper and lower slits intersect at a location 28 for a length "l", as shown in FIG. 3d. The length "l" is preferably ⅓ the thickness "t" to provide a sufficient intersection between the two slits for the insertion of relatively larger diameter catheters. Unlike gaskets of the prior art, both slits extend entirely across the surface of the gasket and open at the side or edge of the gasket. The extension of the slits 26 and 27 across the diameter of the gasket allows the slits to diverge or open wider than prior art valves to permit the insertion of larger catheters than accepted by prior art devices. Moreover, this arrangement of upper and lower slits 26 and 27 permits insertion and removal of the relatively larger catheter while reliably preventing the leakage of blood or air.

The gasket 25 is preferably made of silicone rubber and is sufficiently depressed between the clamping surfaces 23 and 24 to prevent the gasket from collapsing upon insertion of a catheter. In one specific embodiment of the invention, the gasket is composed of a silicone rubber sold under the product name Vesta V420A20. The gasket material has a durometer value of 26-31 so that the gasket material is soft enough to positively seal around the catheter and to resiliently return to the normal configuration with the slits closed and sealed. The gasket material is also sufficient to elastically deform during the introduction of a large catheter without risk of the slits 26 and 27 propagating through the entire thickness "t" of the gasket. The diameter of the gasket of the specific embodiment is 0.39 inches while the thickness is 0.062 inches. As thus configured, the gasket of the one specific embodiment is capable of permitting introduction of a French size 6, 7 or 8 catheter therethrough.

The hemostasis cannula 10 further includes an end retainer 30 that has an internally threaded surface 31 adapted to engage the external threads 15 of the main body 13. The end retainer 30 is adapted to receive and hold a flexible tube 35 to the cannula 10 and includes a tapered surface 32 adapted to engage the flared end 36 of the flexible tube 35. The main body 13 includes a tapered surface 34 that is adapted to at least partially engage the interior tapered surface 42 at the flared end of the flexible tube 35. In assembling the cannula, adhesive or cement is placed on the outside of the flared end 36 of the flexible tube 35 and between the threads 15 of the main body and the threads 31 of the end retainer 30. Thus, as shown in FIG. 1, the flared end 36 of the flexible tube 35 is securely mounted between the tapered surface 34 at the end of the main body 13 and the tapered surface 32 on the inside of the end retainer 30 when the retainer is threaded onto the main body. In the preferred embodiment, the principle parts of the hemostasis cannula 10 are all composed of a suitable rigid plastic material, with the exception of the gasket 25.

In the preferred embodiment, the flexible tube 35 comprises an inner tube 37 opening into the passage 11. A coil body 38, such as a metallic spring, are disposed on the outside of the tube 37. An outer sheath 39 covers the coil body 38. The coil body can be held between the outer sheath 39 and inner tube 37 by shrink fitting, adhesion or a suitable bonding technique to prevent the coil body 38 from migrating relative to the tubing. The coil body 38 is provided to resist crimping, kinking or buckling of the flexible tube 35 during the angiographic procedure. The inner tube 37 and outer sheath 39 are preferably composed of a flexible plastic.

The main body includes a first tapered surface 41 and the flexible tube 35 includes the second tapered surface 42 described above. In the angiographic procedure, a catheter, such as catheter 45 in FIG. 4, is inserted through the opening 21 in the cap 20 and through the flexible gasket 25 at the intersection 28 of the slits 26 and 27. The catheter is directed into the passageway 11 by the first tapered surface 41 and is further directed through the inner tube 37 by the tapered surface 42 of the flexible tube 35 and into the body passageway or blood vessel 49, as shown in FIG. 4. When the catheter is removed from the hemostasis cannula, the upper and lower slits 26 and 27 of the gasket 25 close to prevent blood loss as well as air leakage into the cannula and blood vessel 49. The port 18 of the extension 17 is provided for the introduction of a separate liquid, such as a heparin saline solution.

Referring now to FIGS. 5A, 5B, 5C, 5D and 6, a different and improved embodiment of the device illustrated in FIGS. 1-4 is shown. Specifically, gasket 125 differs from the previously described gasket 25, whereas the remainder of cannula 10 (see FIG. 6) is the same as illustrated and described for FIGS. 1-4.

Gasket 125 is preferably made of silicone rubber and may have similar dimensions as previously described with regard to gasket 25. However, gasket 125 includes slit 126 and slit 127, and further includes a generally axial opening 150 running in between slit 126 and slit 127. Slit 126 is elongated and extends across surface 101 of the gasket and into the gasket toward an opposite surface 102. As seen in FIG. 5B, gasket 125 has an axial thickness 100t. As seen in FIG. 5C, slit 126 has a slit depth 126d, and similarly, slit 127 has a slit depth 127d. Furthermore, axial opening 150 has an axial opening depth 150d. As illustrated, the sum of slit depth 126d, slit depth 127d, and axial opening depth 150d is equal to axial thickness 100t. This provides a resealable path through slit 126, opening 150, and slit 127 for insertion of a catheter through the thickness of gasket 125.

Slit depth 126d is less than thickness 100t; slit depth 127d is less than thickness 100t; and, the sum of depth 126d and 127d is less than axial thickness 100t. Accordingly, slit 126 and slit 127 do not cross each other and do not intersect. Instead, there is elastic material 151 (see FIGS. 5B, 5C) inbetween slit 126 and slit 127. Elastic material 151 is located in the volume of gasket 125 between the two slits and radially around axial opening 150. Thus, in the illustrated embodiment, the central portion of gasket 125 which is axially between the two slits preferably forms a homogeneous disk of elastic material which is interrupted only by axial opening 150 in the central portion thereof.

In the illustrated embodiments, surface 101, surface 102, and the inner edges of slit 126 and of slit 127 are in parallel planes. However, variations of this may be utilized in which these elements are curvalinear and/or lying in planes which are nonparallel. In such embodiments, the dimensions of the thickness, the slit depths, and the axial opening depths may vary according to their location on gasket 125. Accordingly, the present invention may utilize equivalent arrangements to provide the resealable path for insertion of the catheter. For example, although the preferred embodiment utilizes axial opening 150 in the center of gasket 125 coinciding with the axis thereof, it is conceivable that opening 150 could be at an angle and nonparallel to the central axis of gasket 125 and/or be off center.

In the illustrated embodiment of FIGS. 5A-5D, slit depth 126d and slit depth 127d are shown as equal to one another; however they may have a variety of depths. In two specific embodiments of the invention the depth or length 150d of the axial opening is between 0.005 and 0.010 inches. This range of length gives the best results in sealing and freedom of motion. Further dimensions of the two specific embodiments are set forth in the chart below:

|  | Small | Large |
| --- | --- | --- |
| Thickness | .062 in. | .075 in. |
| Diameters | .375 in. | .500 in. |
| Durometers | 30 | 50 |

Figure 8:
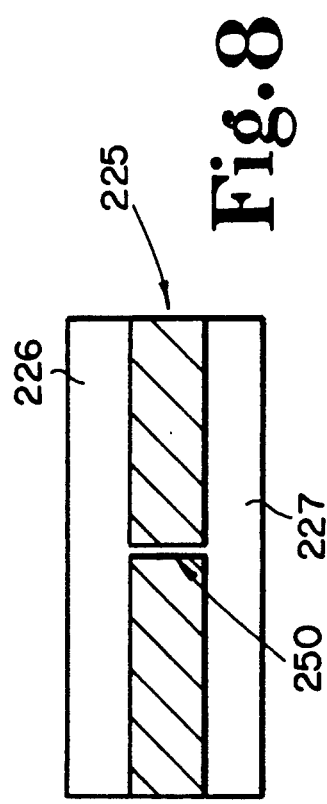
FIG. 8 is a cross-sectional view of the cannula valve gasket of FIG. 7.

Slit 126 and slit 127 preferably are oriented at a 90° angle "X" to each other (see FIG. 5A). However, this angle X may vary according to design including having angle X equal zero degrees with the slits parallel to each other. This is illustrated in FIGS. 7 and 8 with gasket 225 having slit 226 and slit 227 parallel to each other and coplanar with axial opening 250 running inbetween the slits.

Preferably, slit 126 extends across the entire surface 101 so that the ends of slit 126 pass completely through outer edge surface 125a of gasket 125. Similarly, preferably slit 127 extends across the entire surface 102 so that the ends of slit 127 pass completely through outer edge surface 125a. Optionally, slits 126 and 127 may be made so that they do not extend completely through surface 125a, but instead, have a length which is smaller than the diameter of gasket 125 as is done with more conventional slits.

The present invention not only provides excellent sealing characteristics, but is also preferable in that it is easier to manufacture. A blank, disk-like elastic member is provided and then slits 126 and 127 are cut therein diametrically. Axial opening 150 is formed by punching a needle (or similar instrument) through gasket 125 between slit 126 and slit 127. The remainder of cannula 10 is constructed in accordance with FIG. 6 with gasket 125 held in place as previously described.

As before, gasket 125 and gasket 225 are preferably made from a unitary, homogeneous body of flexible, elastic material such as silicone.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, the gasket 25 might be used in a hemostasis cannula not including the reinforcing coil body 38. Additionally, embodiments may be provided having one or more slits parallel to slit 126 and one or more slits parallel to slit 127 with several axial openings therebetween to form a matrix of resealable paths in the gasket.

What is claimed is:

1. A hemostasis cannula comprising:
    a body having an elongated passage therethrough adapted to receive a catheter; and
    a flexible, elastic gasket having an axial thickness and mounted in said passage, including:
        opposite first and second surfaces separated from each other by said axial thickness;
        an elongated first slit extending across said first surface and into said gasket toward said second surface a first slit depth without passing entirely through said gasket;
        an elongated second slit extending across said second surface and into said gasket toward said first surface a second slit depth without passing entirely through said gasket;
        a generally axial opening running inbetween said first slit and said second slit in said gasket an axial opening depth;
        wherein the sum of said first slit depth and said second slit depth is less than said axial thickness so that said gasket includes elastic material axially inbetween said first and second slits; and
        wherein the sum of said first slit depth, said second slit depth and said axial opening depth is equivalent to said axial thickness of said gasket to provide a resealable path for insertion of the catheter through said thickness of said gasket.

2. The hemostasis cannula of claim 1, further comprising a length of flexible tubing in fluid-tight engagement with said body and communicating with one end of said passageway, said tubing including an enclosed coil body extending substantially along said length and adapted to permit bending of said tubing without crimping.

3. The hemostasis cannula of claim 1, wherein said gasket is composed of a silicone rubber material having a durometer softness value of between 26 and 31.

4. The hemostasis cannula of claim 3 wherein said thickness is about 0.062 inches.

5. The hemostasis cannula of claim 3 wherein said gasket has a diameter of 0.390 inches.

6. The hemostasis cannula of claim 4 wherein said gasket has a diameter of 0.390 inches.

7. The hemostasis cannula of claim 1 wherein said first slit extends across the entire first surface so that ends of said first slit pass completely through an outer edge surface of said gasket.

8. The hemostasis cannula of claim 7 wherein said second slit extends across the entire second surface so that ends of said second slit pass completely through an outer edge surface of said gasket.

9. The hemostasis cannula of claim 8 wherein said first slit depth is equivalent to said second slit depth.

10. The hemostasis cannula of claim 8 wherein said axial opening is formed by axially punching a needle through said gasket between said first and second slits.

11. The hemostasis cannula of claim 8 wherein said first and second slit are oriented at an angle to each other.

12. The hemostasis cannula of claim 8 wherein said first and second slit are parallel to each other.

13. The hemostasis cannula of claim 9 wherein said first slit depth is about thirty percent of said axial thickness of said gasket.

14. The hemostasis cannula of claim 1 wherein said first slit depth is about thirty percent of said axial thickness of said gasket.

15. The hemostasis cannula of claim 1 wherein said first and second slit are oriented at an angle to each other.

16. The hemostasis cannula of claim 1 wherein said first and second slit are parallel to each other.

17. A hemostasis cannula comprising:

a body having an elongated passage therethrough adapted to receive a catheter; and a flexible, elastic, disc-like unitary gasket mounted in said passage at one end of said passage, including:

opposite first and second surfaces;

an outer perimetrical edge surface between said first and second surfaces;

an elongated first slit extending across said entire first surface and into said gasket toward said second surface without passing entirely therethrough, said first slit passing both through said first surface and through said outer perimetrical edge surface; and an elongated second slit nonparallel to said first slit and oriented at an angle with respect thereto, said second slit extending across said entire second surface and into said gasket toward said first surface without passing entirely therethrough, said second slit passing both through said second surface and through said outer perimetrical edge surface;

said first and second slits providing a resealable path for insertion of the catheter.

18. The hemostasis cannula of claim 17, further comprising a length of flexible tubing in fluid-tight engagement with said body and communicating with the other end of said passageway, said tubing including an enclosed coil body extending substantially along said length and adapted to permit bending of said tubing without crimping.

19. The hemostasis cannula of claim 17, wherein said gasket is composed of a silicone rubber material having a durometer softness value of between 26 and 31.

20. The hemostasis cannula of claim 19 wherein said gasket has a thickness between said opposite first and second surfaces of 0.062 inches.

21. The hemostasis cannula of claim 19 wherein said gasket has a diameter of 0.390 inches.

22. The hemostasis cannula of claim 20 wherein said gasket has a diameter of 0.390 inches.

* * * * *